(12) United States Patent
Fowler

(10) Patent No.: US 10,039,533 B2
(45) Date of Patent: Aug. 7, 2018

(54) SUPER ELASTIC LOOP EXTRALUMINAL MATERIALS DELIVERY INSTRUMENT

(71) Applicant: Covidien LP, New Haven, CT (US)

(72) Inventor: David Fowler, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 562 days.

(21) Appl. No.: 14/690,805

(22) Filed: Apr. 20, 2015

(65) Prior Publication Data

US 2015/0223794 A1    Aug. 13, 2015

Related U.S. Application Data

(62) Division of application No. 12/270,108, filed on Nov. 13, 2008.

(51) Int. Cl.
    *A61B 17/00*      (2006.01)
    *A61B 17/11*      (2006.01)

(52) U.S. Cl.
    CPC .... *A61B 17/00491* (2013.01); *A61B 17/1114* (2013.01)

(58) Field of Classification Search
    CPC .............. A61B 17/00491; A61B 17/1114
    See application file for complete search history.

(56) References Cited

U.S. PATENT DOCUMENTS

| | | |
|---|---|---|
| 1,642,950 A | 9/1927 | Haas |
| 2,554,352 A | 5/1951 | Ward et al. |
| 2,564,809 A | 8/1951 | Levene |
| 2,623,519 A | 12/1952 | Cohen |
| 2,647,512 A | 8/1953 | Johnson |
| 3,088,207 A | 5/1963 | Borsuk |
| 3,481,323 A | 12/1969 | Cook et al. |
| 3,561,433 A | 2/1971 | Kovach |

(Continued)

FOREIGN PATENT DOCUMENTS

| | | |
|---|---|---|
| EP | 0609020 A1 | 8/1994 |
| WO | 2006/012668 A1 | 2/2006 |
| WO | 2007/021490 A2 | 2/2007 |

OTHER PUBLICATIONS

European Search Report for EP 09252608.6-1269 dated Jan. 7, 2010 (3 pages).

*Primary Examiner* — Lauren P Farrar

(57) ABSTRACT

A materials delivery instrument is provided and includes an outer sheath and an instrument movably mounted within the outer sheath. The instrument includes a treatment lumen extending substantially the length of the instrument for receipt of treatment material. A super elastic wire is positioned in at least a distal end of the instrument. The super elastic wire forms a loop in an unstressed state to allow the instrument to encircle an anastomosis formed between a pair of tubular tissue sections. The super elastic wire is in a stressed state when the instrument is retracted within the outer sheath and in the unstressed state when the instrument is extended from the outer sheath to enclose the anastomosis. A proximal end of the super elastic wire is oriented substantially perpendicular to a plane formed by the loop to allow the instrument to lie parallel to the tubular tissue sections during the spraying of the anastomosis. A source of air pressure may be provided through the instrument to facilitate spraying the treatment material onto the anastomosis.

13 Claims, 6 Drawing Sheets

(56) References Cited

U.S. PATENT DOCUMENTS

| | | |
|---|---|---|
| 3,744,493 A | 7/1973 | Booher et al. |
| 3,934,584 A | 1/1976 | Corio |
| 4,154,239 A | 5/1979 | Turley |
| 4,237,871 A | 12/1980 | Bonnet |
| 4,299,221 A | 11/1981 | Phillips et al. |
| 4,349,028 A | 9/1982 | Green |
| 4,426,024 A | 1/1984 | Hogan et al. |
| 4,522,621 A | 6/1985 | Cassou |
| 4,597,753 A | 7/1986 | Turley |
| 4,665,906 A | 5/1987 | Jervis |
| 4,790,819 A | 12/1988 | Li et al. |
| 4,944,726 A | 7/1990 | Hilal et al. |
| 4,977,900 A | 12/1990 | Fehling et al. |
| 5,015,233 A | 5/1991 | McGough et al. |
| 5,024,656 A | 6/1991 | Gasaway et al. |
| 5,046,486 A | 9/1991 | Grulke et al. |
| 5,049,071 A * | 9/1991 | Davis ................ A61C 17/0202 222/145.5 |
| 5,067,957 A | 11/1991 | Jervis |
| 5,125,836 A | 6/1992 | Dragan et al. |
| 5,129,882 A | 7/1992 | Weldon et al. |
| 5,133,701 A | 7/1992 | Han |
| 5,176,645 A | 1/1993 | Guerrero |
| 5,190,546 A | 3/1993 | Jervis |
| 5,200,170 A | 4/1993 | McDow |
| 5,221,259 A | 6/1993 | Weldon et al. |
| 5,222,939 A | 6/1993 | Tiefenbrun et al. |
| 5,224,931 A | 7/1993 | Kumar |
| 5,312,333 A | 5/1994 | Churinetz et al. |
| 6,524,268 B2 | 2/2003 | Hayner et al. |
| 6,585,717 B1 | 7/2003 | Wittenberger et al. |
| 2002/0082585 A1 * | 6/2002 | Carroll ............ A61M 25/0041 604/528 |
| 2006/0282043 A1 * | 12/2006 | Pyles ................ A61M 25/0041 604/170.03 |
| 2008/0125811 A1 * | 5/2008 | Bettuchi .......... A61B 17/00491 606/214 |

* cited by examiner

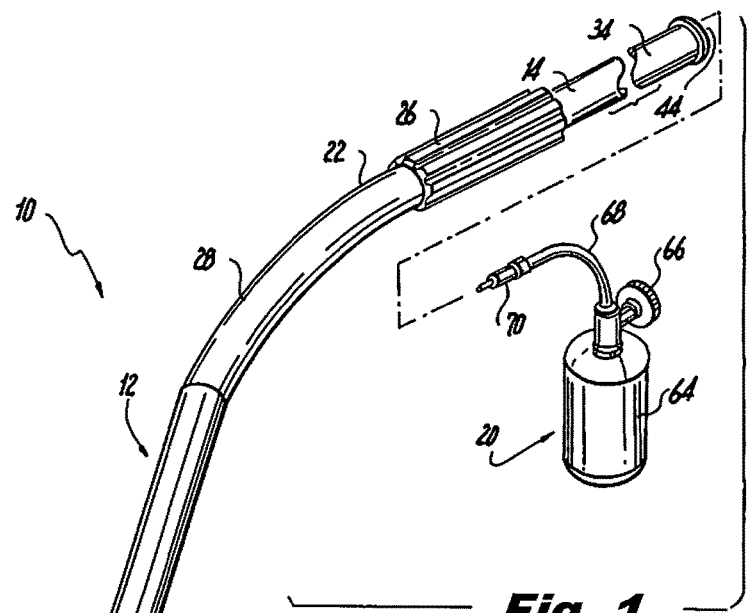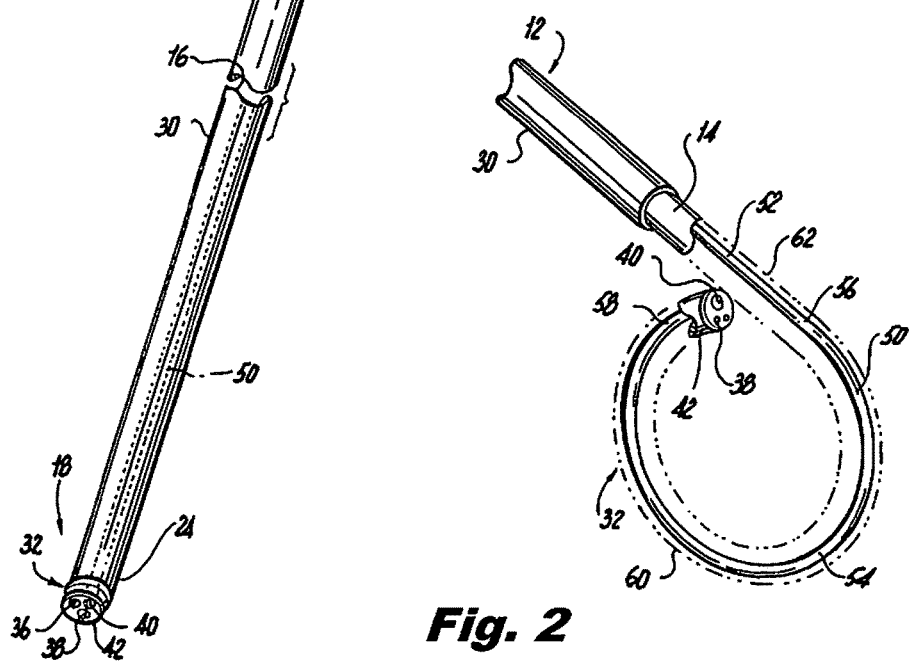

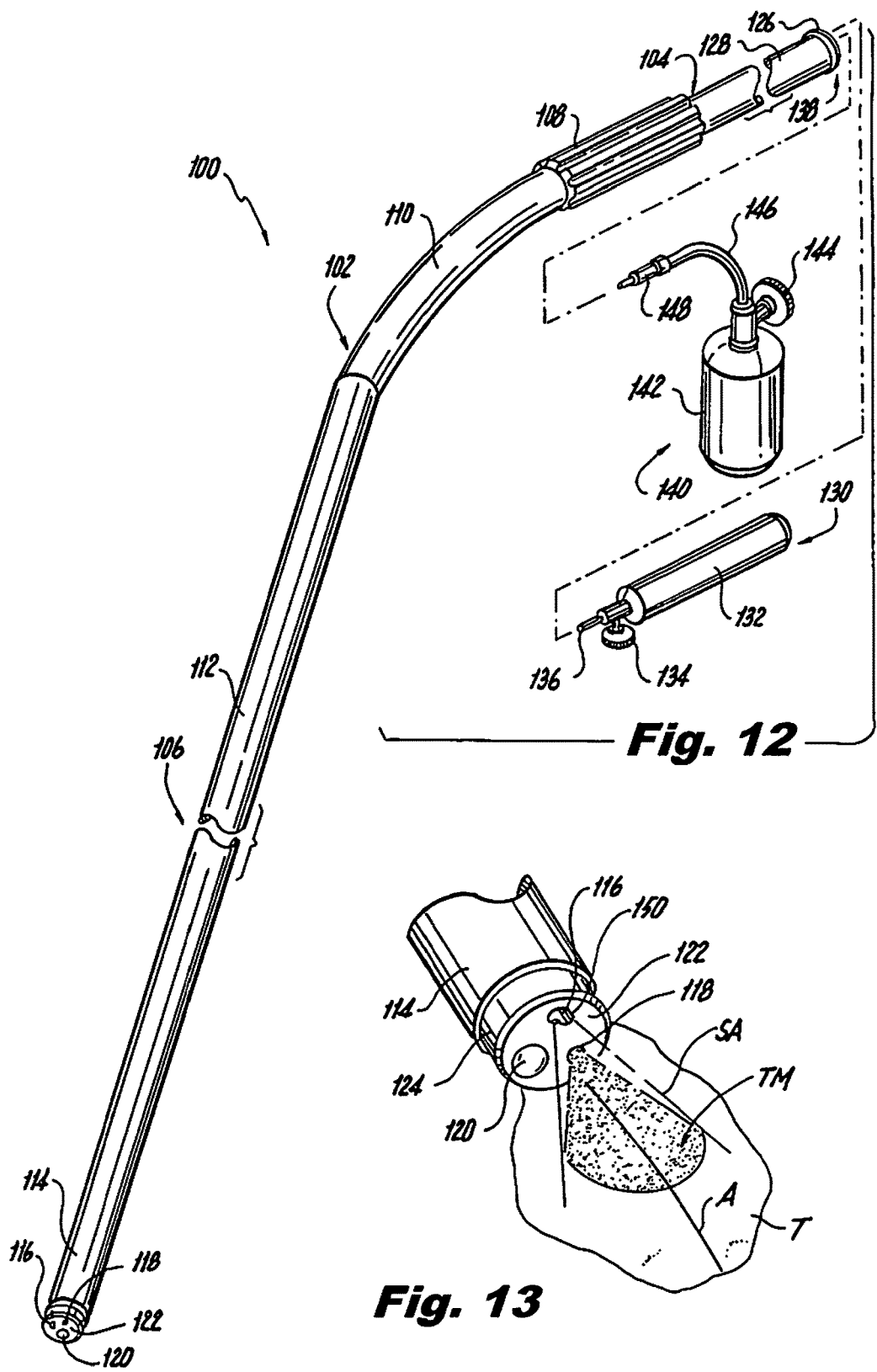

SUPER ELASTIC LOOP EXTRALUMINAL MATERIALS DELIVERY INSTRUMENT

CROSS-REFERENCE TO RELATED APPLICATION

The present application is a divisional application which claims the benefit of and priority to U.S. patent application Ser. No. 12/270,108, filed on Nov. 13, 2008, the contents of which is hereby incorporated by reference in its entirety.

BACKGROUND

1. Technical Field

The present disclosure relates to a materials delivery instrument. More particularly, the present disclosure relates to a materials delivery instrument having a preformed loop of super elastic material for extraluminal delivery of treatment material to the circumference of an anastomotic site.

2. Background of Related Art

Various surgical procedures involve removal of a diseased section of tissue from a tubular tissue or organ and reconnecting the ends of the remaining healthy tubular tissue sections. This is termed forming an anastomosis between the tubular tissue sections. The methods of forming an anastomosis may be loosely grouped into two general categories. In the first category, the fasteners used to rejoin the healthy tubular tissue sections are applied within the lumen defined by the tissue sections while in the second category the fasteners are applied to the exterior of the tissue sections.

In the first category, such as, for example, in colon or bowel surgery, a diseased section of the tissue is excised and the remaining healthy sections of tissue are rejoined. This is typically accomplished by positioning an anvil within one tubular tissue section and a staple head within the opposite tubular tissue section. The free ends of the healthy tissue sections are secured or "purse stringed" radially inwardly adjacent a shaft connecting the anvil to the staple head. The anvil and staple head are then approximated to draw the healthy tubular tissue sections adjacent one another. Thereafter, staples are ejected from the staple head through the inwardly directed edges of the tissues and into the anvil to secure the tissue sections together. Excess tissue extending into the lumens of the tubular tissue sections is cutaway to complete the formation of the anastomosis.

Alternatively, in the second category, when relatively small tubular tissue sections, such as, for example, vascular tissue sections, are being operated upon, the cut free ends of the vascular tissue sections are everted or flared radially outwardly. The radially extending free ends of the tissues are then either stapled or sutured together to form the anastomosis.

When forming an anastomosis in either of the first or second categories, leakage of bodily fluids through gaps in the anastomosis can occur. Further, necrosis or death of substantial amounts of stapled or sutured tissue may occur before the healthy tissues have a chance to heal together resulting in an incomplete anastomosis.

Therefore, a need exists for a materials delivery system capable of applying a sealant or an adhesive to the external circumference of the anastomosis to hold the tissues together during healing. Additionally, a need exists for a delivery system capable of applying a variety of medicaments to the circumference of the anastomosis to facilitate and promote healing.

SUMMARY

There is disclosed a materials delivery instrument including an elongate tube having a treatment lumen. The treatment lumen extends from a proximal end of the instrument and terminates short of the distal end of the instrument. At least one port extends between the treatment lumen and an exterior of the distal end of the instrument. A super elastic wire is positioned within a distal end of the instrument. The super elastic wire has a straight configuration in a stressed condition and a loop configuration in the unstressed condition such that the distal end of the instrument assumes the shape of the super elastic wire for encircling a tubular tissue section.

An outer sheath is movably positioned over the instrument such that the super elastic wire is in the stressed condition when retracted into the sheath and in the unstressed condition when the instrument is extended beyond a distal end of the sheath.

A source of treatment material is provided at a proximal end of the treatment lumen for delivery to the at least one port. In one embodiment, the treatment material is an adhesive. In a specific embodiment, the adhesive is a fibrin glue. In another embodiment, the treatment material is a sealant. In an alternative embodiment, the treatment material is a medicament.

In one embodiment, the super elastic wire is embedded in the distal end of the instrument. In an alternative embodiment, the instrument includes a shaping lumen located within the distal end of the instrument and the super elastic wire is positioned within the shaping lumen.

In another embodiment, the super elastic wire has a proximal portion oriented perpendicular to a plane defined by the loop when the super elastic wire is in the unstressed condition.

There is also disclosed a materials delivery instrument including an elongate tube having a treatment lumen for receipt of treatment material therethrough. The treatment lumen extends from a proximal end of the instrument to a distal end of the instrument. An auxiliary lumen is provided for receipt of air pressure and extends from a proximal end of the instrument to the distal end of the instrument. A super elastic wire is positioned within a distal end of the instrument. The super elastic wire has a straight configuration in a stressed condition and a loop-shaped configuration in the unstressed condition such that the distal end of the instrument assumes the shape of the super elastic wire for encircling a tubular tissue section.

An outer sheath is movably positioned over the instrument such that the super elastic wire is in the stressed condition when retracted into the sheath and in the unstressed condition when the instrument is extended beyond a distal end of the sheath.

In one embodiment, a deflector is positioned adjacent the distal end of the auxiliary lumen for directing airflow towards treatment material ejected from a distal end of the treatment lumen.

In one embodiment, a shaping lumen is formed within the distal end of the instrument such that the super elastic wire is positioned within the shaping lumen.

In a specific embodiment, the super elastic wire has a proximal portion oriented substantially perpendicular to a plane defined by the loop when the super elastic wire is in the unstressed condition.

There is also disclosed a method of delivering treatment material to an anastomosis formed between a pair of tubular tissue sections. The method includes providing a materials delivery instrument including an elongate tube having a treatment lumen, the treatment lumen extending from a proximal end of the instrument and toward a distal end of the instrument; at least one port extending between the treatment lumen and an exterior of the distal end of the instrument; a super elastic wire positioned within a distal end of the instrument, the super elastic wire having a straight configuration in a stressed condition and a loop-shaped configuration in an unstressed condition such that the distal end of the instrument assumes the shape of the super elastic wire for encircling a tubular tissue section; and an outer sheath movably positioned over the instrument such that the super elastic wire is in the stressed condition when the instrument is retracted into the sheath and in the unstressed condition when the instrument is extended beyond a distal end of the sheath.

The method includes the steps of positioning a distal end of the materials delivery instrument adjacent an anastomosis formed between a pair of tubular tissue sections and extending the instrument beyond the distal end of the sheath to release the super elastic wire from the stressed condition to the unstressed condition such that the instrument encircles the anastomosis. Thereafter, treatment material is sprayed out of the at least one port and onto the outer surface of the anastomosis.

In one embodiment, the at least one port extends through a side wall in the instrument and the treatment material is sprayed through the at least one port and onto the entire outer circumference of the anastomosis simultaneously.

In an alternative embodiment, the treatment material is progressively sprayed onto the anastomosis as the instrument is extended from the sheath and around the anastomosis.

In a further alternative embodiment, the treatment material is sprayed onto the anastomosis as the instrument is refracted back into the sheath.

In a still further alternative embodiment, the distal end of the materials delivery instrument is positioned substantially perpendicular to the tubular tissue sections and reoriented substantially parallel to the tubular tissue sections prior to spraying the treatment material onto the anastomosis.

DESCRIPTION OF THE DRAWINGS

Various embodiments of the presently disclosed materials delivery instrument are disclosed herein with reference to the drawings, wherein:

FIG. 1 is a perspective view of one embodiment of a materials delivery instrument;

FIG. 2 is a perspective view, with parts removed, of the materials delivery instrument of FIG. 1 with a portion of the materials delivery instrument extended out of a sheath of the materials delivery instrument;

FIG. 12 is a perspective view of an alternative embodiment of a materials delivery instrument;

FIG. 13 is an enlarged view of the distal end of the materials delivery instrument of FIG. 12;

DETAILED DESCRIPTION OF EMBODIMENTS

Figure 3:
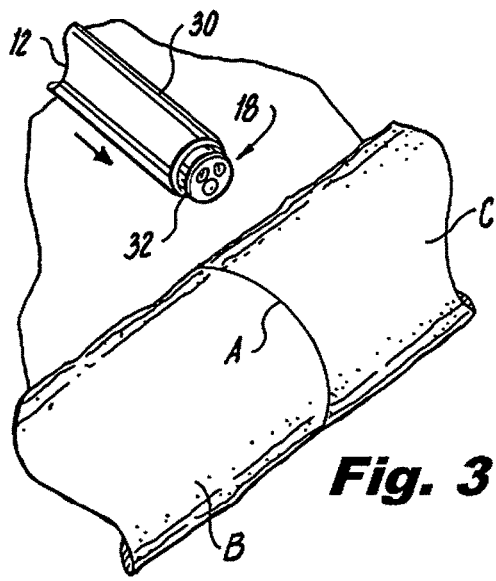
FIG. 3 is a perspective view of the distal end of the materials delivery instrument positioned adjacent an anastomosis formed between a pair of tubular tissue sections.
Figure 4:
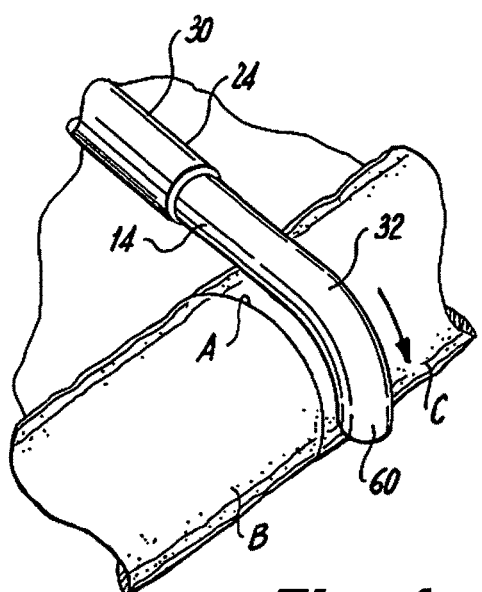
FIG. 4 is a perspective view of the instrument initially encircling the anastomosis between the tubular tissue sections.

Embodiments of the presently disclosed materials delivery instrument will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Referring to FIG. 1, there is disclosed a materials delivery instrument 10 for extraluminal delivery of treatment material to the circumference of an anastomosis formed between two tubular tissue sections. Materials delivery instrument at 10 generally includes an outer sheath 12 and an elongate tubular member 14 movably mounted within a lumen 16 of outer sheath 12. Materials delivery instrument 10 includes a distal end 18 which is positionable adjacent the anastomosis in order to deliver the treatment material to a circumference of the anastomosis as described in more detail hereinbelow. A source of treatment material 20 is provided for use with materials delivery instrument 10.

Lumen 16 of outer sheath 12 extends from a proximal end 22 of outer sheath 12 to a distal end 24 of outer sheath 12. A handle 26 is formed on proximal end 22 of outer sheath 12 to move outer sheath 12 relative to elongate tubular member 14. A relatively flexible center portion 28 extends distally from handle 26 to facilitate manipulation of materials delivery instrument 10 within the body of a patient. A relatively rigid distal portion 30 of outer sheath 12 extends distally from flexible center portion 28 of outer sheath 12. Rigid distal portion 30 is provided to restrain a distal portion 32 of elongate tubular member 14 when elongate tubular member 14 is in a proximal position relative to outer sheath 12 and to release distal portion 32 of elongate tubular member 14 when elongate tubular member 14 is moved distally relative to outer sheath 12. A proximal end 34 of elongate tubular member 14 is configured to receive source of treatment material 20.

Referring to FIGS. 1 and 2, a plurality of lumens, such as an auxiliary or first lumen 36, a treatment or second lumen 38 and a shaping or third lumen 40 are provided within elongate tubular member 14. First lumen 36 extends completely from proximal end 34 of elongate tubular member 14 to a distal end 42 of elongate tubular member 14. First lumen 36 is provided to accommodate various auxiliary functions such as, for example, a source of air pressure, optical devices, cautery devices etc.

Figure 6:
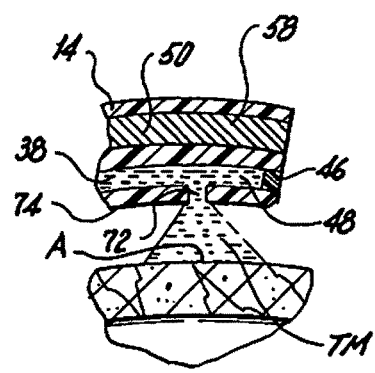
FIG. 6 is a cross-sectional view taken along line 6-6 of FIG. 5.

Second lumen 38 is provided to receive source of treatment fluid 20 at a proximal end 44 thereof. Referring for the moment to FIG. 6, second lumen 38 includes a plug 46 positioned within a distal end 48 of second lumen 38 in order to seal distal end 48.

With continued reference to FIGS. 1 and 2, third lumen 40 extends proximally from distal end 42 of elongate tubular member 14 and is configured to receive a super elastic structure or wire 50 formed from a shape memory alloy. The nature of a shape memory alloy allows the alloy to retain a preformed state or shape when the alloy is in an unstressed or unrestrained condition and allows the alloy to be deformed to another shape by restraining the alloy in a stressed condition. Super elastic wire 50 may be formed from various shapes of materials such as, for example, round wire, rectangular wire, sheet alloys, etc. Super elastic wire 50 is provided to configure the shape of distal portion 32 of elongate tubular member 14 as distal portion 32 is extended beyond distal end 24 of outer sheath 12.

As the best shown in FIG. 1, and as noted above, super elastic wire 50 is positioned within third lumen 40 formed in distal portion 32 of elongate tubular member 14. As shown, when distal portion 32 of elongate tubular member 14 is retracted within rigid distal portion 30 of outer sheath 12, super elastic wire 50 is restrained in a relatively straight shape or stressed condition. It should be noted that, while super elastic wire is disclosed as being positioned within third lumen 40 of elongate tubular member 14, it is also contemplated that super elastic wire 50 may be embedded directly into the elongate tubular member 14 or a portion thereof.

Referring now to FIG. 2, in the unstressed or unrestrained condition, super elastic wire 50 includes a relatively straight proximal portion 52 and an encircling or loop portion 54 extending distally from a distal end 56 of straight proximal portion 52. A distal end 58 of loop portion 54 terminates within third lumen 40 at distal end 42 of elongate tubular member 14. Since super elastic wire 50 is located within distal end 42 of elongate tubular member 14, and the tube is formed from a relatively flexible material, distal end 42 assumes the shape of super elastic wire 50 when it is in the stressed and unstressed conditions. Specifically, when super elastic wire 50 is in the preformed and unstressed condition, loop portion 54 of super elastic wire 50 configures distal end 42 of elongate tubular member 14 into a loop portion 60 while a proximal straight portion 62 of elongate tubular member 14 conforms to relatively straight proximal portion 52 of super elastic wire 50. Loop portion 60 of elongate tubular member 14, conforming to the shape of loop portion 54 of super elastic wire 50, is provided to encircle the anastomosis formed between two tubular tissue sections to facilitate the application of a treatment material to the entire circumference of the anastomosis.

Referring now to FIGS. 1 and 3-6, the use of materials delivery instrument 10 to apply a treatment material circumferentially to an anastomosis formed between a pair of tubular tissue sections will now be described. Referring initially to FIG. 1, and as described herein above, source of treatment material 20 is provided for use with materials delivery instrument 10. Source of treatment material 20 generally includes a pressurized canister 64 containing the treatment material. A valve 66 is provided on canister 64 to control the flow of the treatment material out of canister 64. A tube 68 extends from valve 66 and terminates in a connector 70 which is configured to engage proximal end 44 of second lumen 38 to supply the treatment material through second lumen 38 to distal end 42 of elongate tubular member 14 for application to the anastomosis. Other sources can be used, such as pumped, compressible chambers, or plunger-driven sources to drive material to the materials delivery instrument.

Elongate tubular member 14 is initially in a retracted position relative to outer sheath 12 such that super elastic wire 50 and thus distal portion 32 are restrained in a relatively straight configuration within rigid distal portion 30 of outer sheath 12.

Referring to FIG. 3, distal end 18 of materials delivery instrument 10 is initially positioned adjacent an anastomosis A formed between a pair of tubular tissue sections B and C. Thereafter, elongate tubular member 14 is advanced distally through outer sheath 12 (FIG. 1) causing distal portion 32 of elongate tubular member 14 to extend distally out of rigid distal portion 30 of outer sheath 12. As distal portion 32 of elongate tubular member 14 extends out of distal portion 30, super elastic wire 50 and distal portion 32 begin to return to the unstressed state or condition. Thus, distal portion 32 begins to transform to a loop-shaped portion 60 to initially begin encircling anastomosis A.

Figure 5:
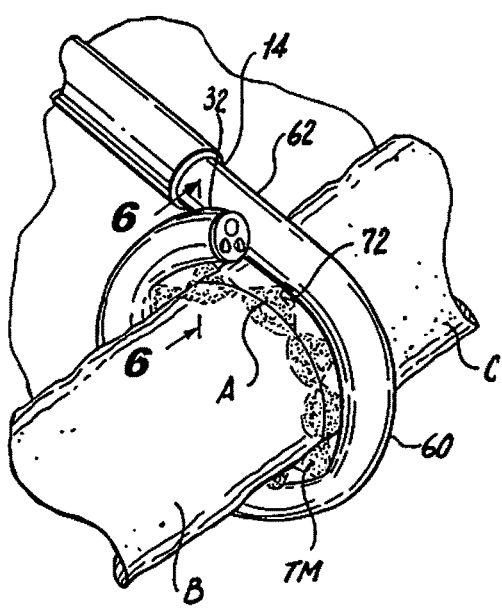
FIG. 5 is a perspective view of the instrument completely encircling the anastomosis between the tubular tissue sections and spraying treatment material onto the anastomosis.

Referring now to FIG. 5, when distal portion 32 of elongate tubular member 14 has been completely extended out of rigid distal portion 30 of outer sheath 12, loop 60 is fully formed about the circumference of anastomosis A. Distal portion 32 of elongate tubular member 14 is now in a configuration to apply a treatment material TM to the circumference of the anastomosis. Valve 66 is opened to allow treatment material TM to flow from canister 64 through tube 68 and second lumen 38. Referring to FIGS. 5 and 6, a plurality of ports 72 are in fluid communication with distal end 48 of second lumen 38. The loop 60 desirably extends around a 360 degree circle, in certain embodiments. However, some embodiments according to the present disclosure include a loop-shaped portion that is arcuately shaped and extends around less than 360 degrees.

With specific reference to FIG. 6, ports 72 extend through a sidewall 74 formed in distal portion 32 of elongate tubular member 14. Ports 72 are in fluid communication within second lumen 38 so as to discharge or spray treatment material TM onto anastomosis A. As noted herein above, second lumen 38 is sealed at distal end 48 by plug 46. Once valve 46 is opened, treatment material TM is released from canister 64 through second lumen 38 and ports 72 and is simultaneously sprayed on to the entire circumference of anastomosis A. Thus, the use of super elastic wire 50 to configure distal portion 32 of elongate tubular member 14 into a loop portion 60 enables materials delivery instrument 10 to simultaneously spray the entire circumference of anastomosis A with the various treatment materials TM's described above, such as sealants, adhesives, or medicaments. Once anastomosis A has been covered with the desired treatment material TM, proximal end 44 (FIG. 1) of elongate tubular member 14 may be drawn proximally within outer sheath 12 to retract distal portion 32 of elongate tubular member 14 back within rigid distal portion 30 of outer sheath 12 thereby returning super elastic wire 50 to the relatively straight or stressed condition within rigid distal end 30 of outer sheath 12.

Figure 7:
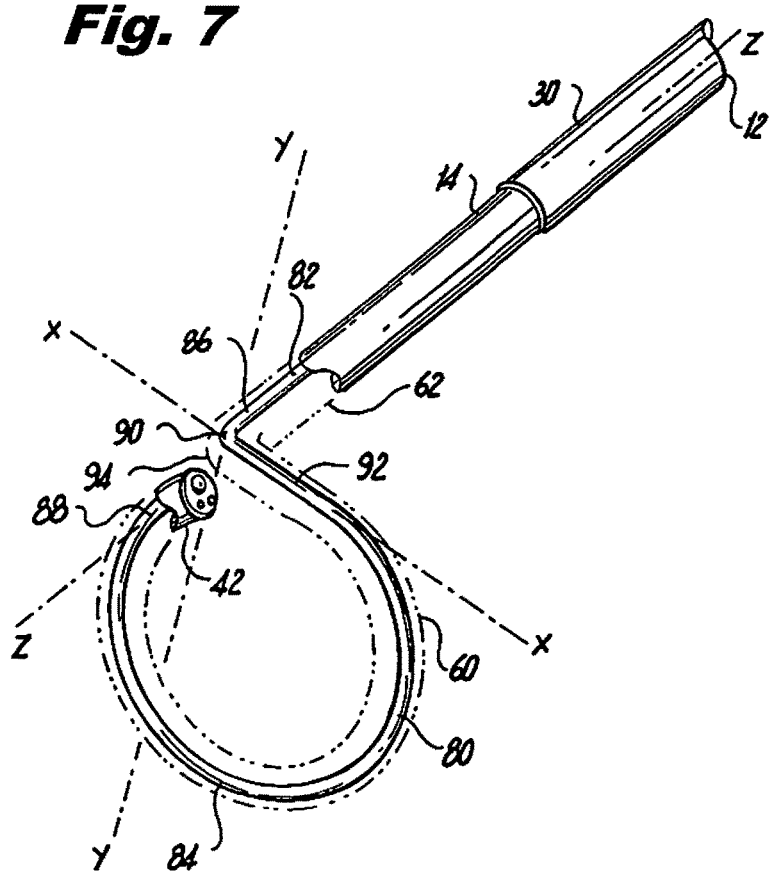
FIG. 7 is a perspective view, partially shown in section, of an alternative embodiment of a super elastic wire for use in the materials delivery instrument of FIG. 1.

Referring now to FIG. 7, there is disclosed an alternative embodiment of a super elastic wire 80 for use with materials delivery instrument 10. Super elastic wire 80 is configured to orient proximal straight portion 62 of elongate tubular member 14 perpendicularly to loop portion 60 of elongate tubular member 14 in order to better visualize the circumference of the anastomosis during the spraying of the treatment material onto the anastomosis. Super elastic wire 80 generally includes a relatively straight proximal portion 82 and an encircling or loop portion 84 extending distally from distal end 86 of proximal portion 82. Loop portion 84 terminates in a distal end 88 located adjacent distal end 42 of elongate tubular member 14. In this embodiment, a substantially right angle or 90° bend 90 is formed between distal end 86 of straight portion 82 and a proximal end 92 of loop portion 84. In the unstressed condition, this results in the formation of a substantially right angle or 90° bend 94 between straight portion 62 elongate tubular member 14 and loop portion 60 of tubular member 14. Thus, loop portion 60 of elongate tubular member 14 is formed within the plane X-Y while relatively straight portion 62 of elongate tubular member 14 extends perpendicular to loop portion 60 along axis Z-Z.

Figure 8:
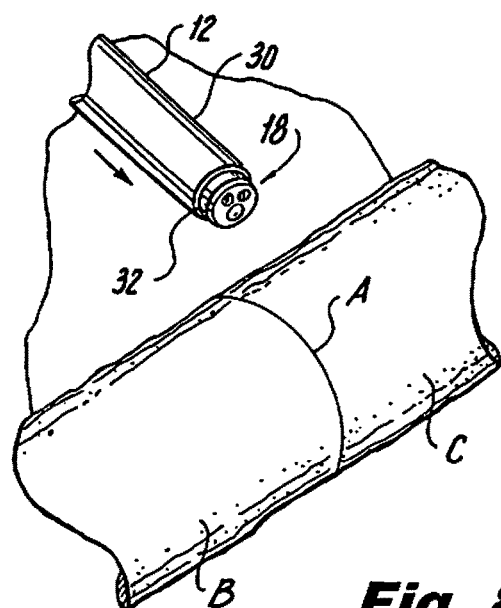
FIG. 8 is a perspective view of the materials delivery instrument of FIG. 7 initially positioned adjacent the anastomosis formed between a pair of tubular tissue sections.

Referring now to FIGS. 1 and 8-11, the use of materials delivery instrument 10, incorporating super elastic wire 80, to apply a treatment material to the circumference of anastomosis A formed between tubular tissue sections B and C will now be described. Referring initially to FIG. 1, materials delivery instrument 10 is in an initial position with elongate tubular member 14 in a proximal most position within outer sheath 12 such that rigid distal portion 30 of outer sheath 12 restrains super elastic wire 80 in a relatively straight or stressed condition within rigid distal portion 30. As best shown in FIG. 8, distal end 18 of materials delivery instrument 10 is positioned adjacent anastomosis A formed between first and second tubular tissue sections B and C, respectively.

Figure 9:
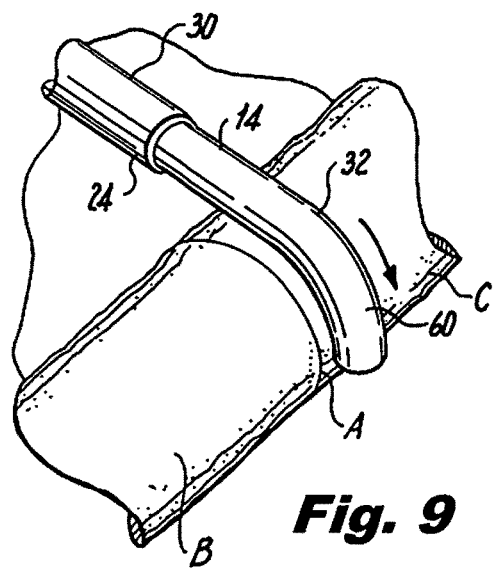
FIG. 9 is a perspective view of the materials delivery instrument of FIG. 7 initially encircling the anastomosis.
Figure 10:
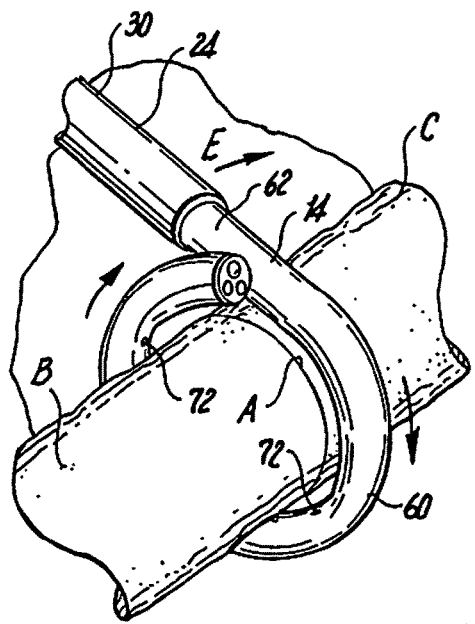
FIG. 10 is a perspective view of the materials delivery instrument of FIG. 7 completely encircling the anastomosis.

As best shown in FIGS. 9 and 10, distal portion 32 of elongate tubular member 14 is initially advanced out of distal end 24 of outer sheath 12 to initially begin to form loop 60 in distal portion 32 about the circumference of anastomosis A (FIG. 9). Continued advancement of distal portion 32 fully forms loop 60 about the circumference of anastomosis A (FIG. 10).

Figure 11:
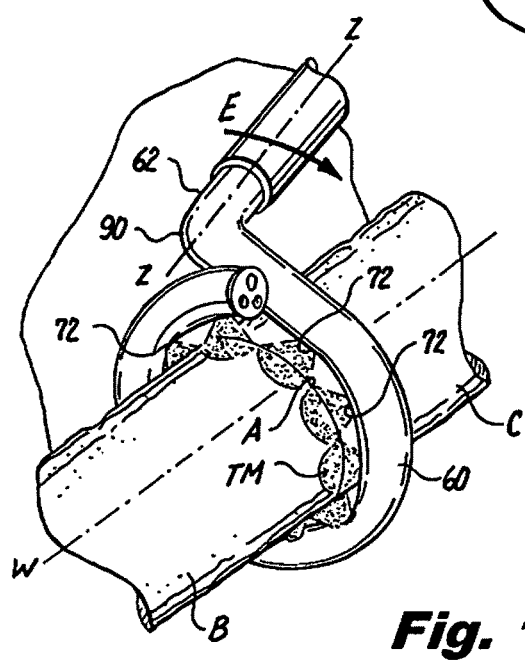
FIG. 11 is a perspective view of the materials delivery instrument of FIG. 7 partially reoriented parallel to the tubular tissue sections and spraying treatment material onto the anastomosis.
Figure 14:
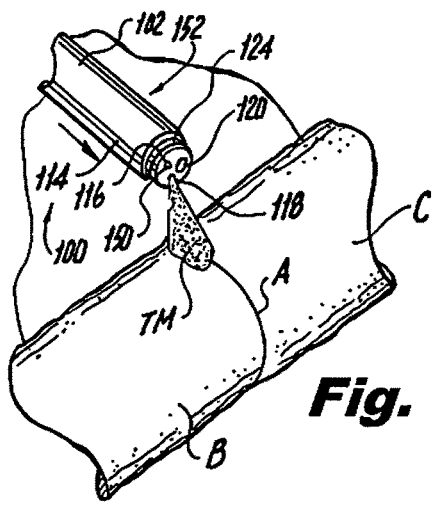
FIG. 14 is a perspective view of the distal end of the materials delivery instrument of FIG. 12 initially positioned adjacent an anastomosis formed between a pair of tubular tissue sections and initially spraying treatment material from the instrument onto the anastomosis.

Referring now to FIGS. 10 and 11, once loop 60 has been fully formed and completely encircles anastomosis A, continued advancement of straight portion 62 of elongate tubular member 14 out of rigid distal portion 30 of outer sheath 12 further releases super elastic wire 80 from the restrained condition to the un-restrained condition allowing bend 90 to be formed between straight portion 82 and loop portion 84 of super elastic wire 80. This causes bend 94 to form in elongate tubular member 14 between loop portion 60 of elongate tubular member 14 and straight portion 62 of elongate tubular member 14. Specifically, straight portion 62 of elongate tubular member 14 moves in the direction of arrow E from an orientation perpendicular to a longitudinal axis W-W of tubular tissue sections B and C to an orientation wherein the longitudinal axis Z-Z straight portion 62 lies substantially parallel to longitudinal axis W-W of tubular tissue sections B and C. This allows better visualization of anastomosis A during the application of treatment material TM to anastomosis A.

Referring specifically to FIG. 11, once elongate tubular member 14, and specifically loop 60, has been properly positioned about anastomosis A, treatment material TM is sprayed simultaneously through all ports 72 onto the full circumference of anastomosis A.

Referring now to FIG. 12, there is disclosed an alternative embodiment of a materials delivery instrument 100 which is substantially similar to materials delivery instrument 10 described herein above. Materials delivery instrument 100 generally includes an outer sheath 102 and an instrument 104 extending through a lumen 106 of outer sheath 102. Outer sheath 102 includes a handle 108 having a flexible center portion 110 extending distally from handle 108. A relatively rigid distal portion 112 extends distally from flexible center portion 110. Lumen 106 extends from handle 108 to a distal end 114 of rigid distal portion 112.

Instrument 104 is similar to elongate tubular member 14 described herein above and includes an auxiliary or first lumen 116, a treatment or second lumen 118 and a shaping or third lumen 120. First lumen 116 is open to a distal end face 122 formed in distal end 124 of instrument 104 and extends through instrument 104 to a proximal opening 126 formed in proximal end 128 of instrument 104. First lumen 116 is provided to receive a source of air pressure such as source of air pressure 130 therethrough to assist in spraying treatment material on the tissue. Source of air pressure 130 generally includes a canister of pressurized air 132 and a valve 134 to control the release of air pressure from canister 132. A connector 136 is provided on valve 134 and is configured to engage proximal opening 138 of first lumen 116.

Second lumen 118 is also open to distal end face 122 and extends through instrument 104 to a proximal opening 138. Second lumen 118 is provided to receive a source of treatment material 140 which is substantially identical to source of treatment material 20 described herein above with respect to materials delivery instrument 10. Source of treatment material 140 generally includes a pressurized canister 142 containing the treatment material and a valve 144 provided on canister 142 for controlling the flow of treatment material out of canister 142, or another source, as discussed above. A tube 146 extends from valve 144 and terminates in a connector 148 configured to engage proximal opening 138 of second lumen 118.

Third lumen 120 is configured to receive a super elastic wire substantially identical to super elastic wire 50 described herein above with respect to materials delivery instrument 10 and as described in more detail here and below.

Referring now to FIG. 13, a shield or deflector 150 is provided on end face 122 adjacent first lumen 116. Deflector 150 is provided to direct a stream of airflow SA, received through first lumen 116 from source of air pressure 130, into treatment material TM ejected from second lumen 118 to facilitate atomizing and uniformly spraying treatment material TM onto the desired tissue T.

Referring now to FIGS. 12 and 14-18, and initially with respect to FIG. 12, the use of materials delivery instrument 100 to spray treatment material TM onto an anastomosis A formed between a pair of tubular tissue sections B and C will now be described. In the initial position, instrument 104 is in a proximal most position within the outer sheath 102. Source of treatment fluid 140 is connected to proximal opening 138 of second lumen 118 and source of air pressure 130 is connected to proximal opening 126 of first lumen 116. Referring now to FIG. 14, initially, a distal end 152 of materials delivery instrument 100 is positioned adjacent anastomosis A. Valve 144 on source of treatment material 140 (FIG. 12) is opened to force treatment material TM out of second lumen 118 towards anastomosis A. Likewise, valve 134 on source of air pressure 130 (FIG. 12) is opened to force stream of airflow SA through first lumen 116 and out of distal end face 122 of instrument 104. As stream of airflow SA exits distal end face 122 it engages, and is directed by, deflector 150 towards treatment material TM to atomize treatment material TM and provide a uniform pattern of treatment material TM as it is applied to anastomosis A.

Figure 15:
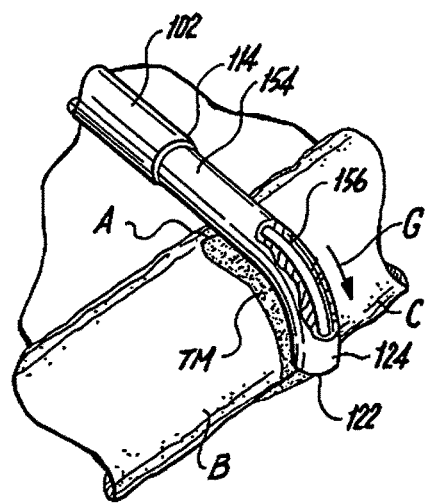
FIG. 15 is a perspective view of the instrument of the materials delivery instrument being advanced around the anastomosis to spray treatment material onto the anastomosis.

Referring now to FIG. 15, instrument 104 is moved distally relative to outer sheath 102 allowing a distal portion 154 of instrument 104 to move distally relative to distal end 114 of outer sheath 102. As noted herein above, instrument 104 is similar to elongate tubular member 14 described herein above and includes a super elastic wire 156 positioned within third lumen 120 in distal end portion 154 of instrument 104. Super elastic wire 156 is identical to super elastic wire 50 described herein above and is provided to shape distal portion 154 into a loop configuration in a manner identical to that described herein above with respect to loop proportion 60 of elongate tubular member 14. As distal and portion 154 of instrument 104 is advanced in the direction of the arrow G, treatment material TM, assisted by stream of airflow SA, continues to be sprayed out of end face 122 in distal end 124 of elongate tubular member 104 and onto anastomosis A.

Figure 16:
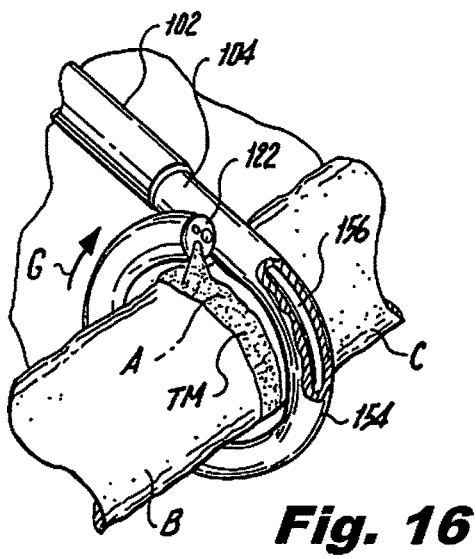
FIG. 16 is a perspective view of the instrument completely encircling the anastomosis to spray a complete circle of treatment material onto the anastomosis.

As best shown in FIG. 16, continued advancement of distal portion 154 in the direction of arrow G results in the formation of a line of treatment material TM about the complete conference of anastomosis A. Thus, materials delivery instrument 100 is configured to progressively spray treatment material TM about the circumference of anastomosis A as distal portion 154 is advanced around anastomosis A. This allows the surgeon to stop, or reorient the direction of, the sprayed treatment material TM during the application to anastomosis A to ensure that treatment material TM is accurately and uniformly sprayed onto the circumference of anastomosis A.

Figure 17:
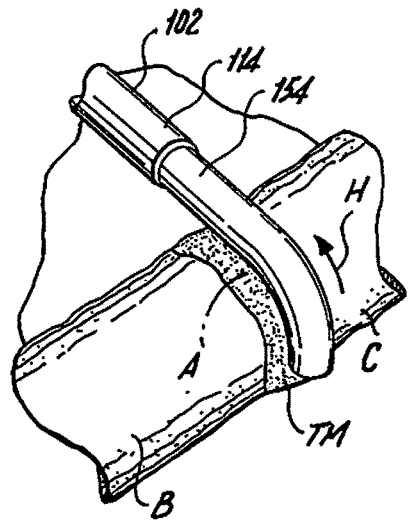
FIG. 17 is a perspective view of the instrument being retracted back around the anastomosis to spray a second coat of treatment material onto the anastomosis.
Figure 18:
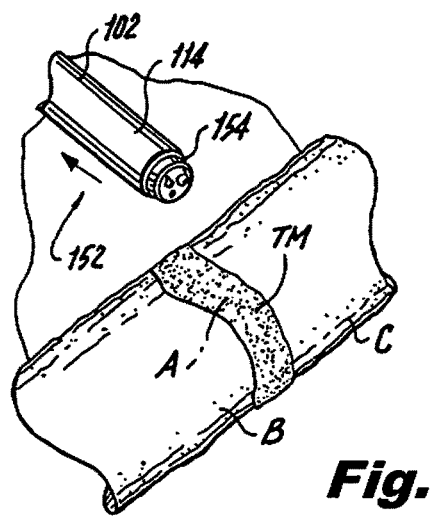
FIG. 18 is a perspective view of the instrument, retracted into the catheter sheath, and being withdrawn from the anastomosis site.

Referring now to FIGS. 17 and 18, in order to deliver a more complete and uniform application of treatment material TM to anastomosis A, treatment material TM, assisted by source of airflow SA, may continue to be sprayed over the previously applied layer of treatment material TM upon retraction of distal portion 154 back around anastomosis A in the direction of arrow H and into distal end 114 of outer sheath 102. Alternatively, distal portion 154 may be advanced in the direction of arrow G (FIGS. 15 and 16) about the circumference of anastomosis A prior to the discharge of treatment material TM and initiating and completely spraying treatment material TM, assisted by source of airflow SA, onto anastomosis A as distal portion 154 is retracted in the direction of arrow H.

Thus, materials delivery instrument 100 provides the ability to progressively spray treatment material TM onto anastomosis A both as distal portion 154 it is advanced to form a loop about anastomosis A and as distal portion 154 is retracted from around anastomosis A. Alternatively, the spraying of treatment material TM may be stopped and reoriented in either direction to more accurately apply treatment material TM to anastomosis A. As noted herein above, this allows the surgeon to ensure that a complete and uniform layer of treatment material TM is applied to anastomosis A.

In a further embodiment of the present disclosure, the materials delivery instrument may be used intra luminally. Ports are disposed on an exterior side of the elongate tubular member so as to discharge the material outwardly. The instrument may otherwise be as described in FIGS. 1-6.

It will be understood that various modifications may be made to the embodiments disclosed herein. For example, and as noted herein above, the disclosed super elastic wire may either be contained within a lumen of the disclosed instrument or maybe directly embedded within the distal end of the disclosed instrument. Further, the preformed shape of the super elastic wire may assume other configurations such as, for example, spiral, oval, etc. Additionally, further additional lumens may be provided within the disclosed instrument to accommodate various other functions such as, for example, the provision of optical devices, electrocautery devices, etc. Therefore, the above description should not be construed as limiting, but merely as exemplifications of particular embodiments. Those skilled in the art will envision other modifications within the scope and spirit of the claims appended hereto.

The invention claimed is:

1. A method of delivering treatment material to an anastomosis formed between a pair of tubular tissue sections comprising:
   providing an instrument including:
      an elongate tube having a treatment lumen, the treatment lumen extending from a proximal end of the instrument and toward a distal end of the instrument;
      an auxiliary lumen extending between the proximal end of the instrument and the distal end of the instrument;
      a deflector disposed at the distal end of the instrument and operatively coupled to the auxiliary lumen;
      a port extending between the treatment lumen and an exterior of the distal end of the instrument; and
      a super elastic wire positioned within a distal end of the instrument, the super elastic wire having a straight configuration in a stressed condition and a loop configuration in an unstressed condition such that the distal end of the instrument assumes the shape of the super elastic wire for encircling a tubular tissue section;
   providing a sheath movably positioned over the instrument such that the super elastic wire is in the stressed condition when the instrument is retracted into the sheath and in the unstressed condition when the instrument is extended beyond a distal end of the sheath;
   positioning a distal end of the instrument adjacent the anastomosis formed between the pair of tubular tissue sections;
   extending the instrument beyond the distal end of the sheath to release the super elastic wire from the stressed condition to the unstressed condition such that the instrument encircles the anastomosis;
   directing airflow through the auxiliary lumen and past the deflector such that the airflow is directed towards the port; and
   spraying treatment material out of the port and onto the anastomosis, such that the airflow directed by the deflector facilitates disbursement of the treatment material.

2. The method as recited in claim 1, wherein the port extends through a side wall in the instrument and the treatment material is sprayed through the port and onto the anastomosis.

3. The method as recited in claim 1, wherein the treatment material is sprayed onto the anastomosis as the instrument is extended from the sheath and around the anastomosis.

4. The method as recited in claim 1, wherein the treatment material is sprayed onto the anastomosis as the instrument is retracted back into the sheath.

5. The method as recited in claim 1, further comprising positioning the distal end of the instrument substantially perpendicular to the tubular tissue sections and reorienting the instrument substantially parallel to the tubular tissue sections prior to spraying the treatment material onto the anastomosis.

6. The method as recited in claim 1, wherein providing the instrument further includes providing a source of treatment material at a proximal end of the treatment lumen for delivery to the port.

7. The method as recited in claim 1, wherein spraying treatment material out of the port and onto the anastomosis includes spraying a material selected from the group consisting of an adhesive, a fibrin glue, a sealant, and a medicament.

8. The method as recited in claim 1, wherein providing the instrument further includes providing the deflector on a distal end face of the instrument.

9. The method as recited in claim 1, wherein providing the instrument further includes providing the deflector adjacent the distal end of the auxiliary lumen.

10. The method as recited in claim 1, wherein spraying treatment material out of the port and onto the anastomosis further includes, providing air pressure at the proximal end of the auxiliary lumen, creating airflow at the distal end of the auxiliary lumen, and directing the airflow into treatment material ejected from the port, the deflector configured to uniformly disburse the treatment material upon the tubular tissue.

11. The method as recited in claim 1, wherein spraying treatment material out of the port and onto the anastomosis further includes atomizing the treatment material using the airflow directed by the deflector.

12. A method of delivering treatment material to an anastomosis formed between a pair of tubular tissue sections, the method comprising:

positioning a distal end of an instrument including an elongate tube and a treatment lumen adjacent the anastomosis;

extending the instrument beyond a distal end of a sheath positioned over the instrument to release a super elastic wire positioned within the distal end of the instrument from a stressed condition, when the instrument is positioned within the sheath, to an unstressed condition, when the instrument is extended beyond the distal end of the sheath, such that the instrument encircles the anastomosis;

directing airflow through an auxiliary lumen extending between a proximal end of the instrument and the distal end of the instrument, and past a deflector disposed at the distal end of the instrument, such that the airflow is directed towards a port extending between the treatment lumen and an exterior of the distal end of the instrument; and spraying treatment material out of the port and onto the anastomosis, such that the airflow directed by the deflector facilitates disbursement of the treatment material.

13. The method as recited in claim 12, wherein spraying treatment material out of the port and onto the anastomosis includes spraying a material selected from the group consisting of an adhesive, a fibrin glue, and a sealant.

\* \* \* \* \*